(12) United States Patent
Chikovani et al.

(10) Patent No.: US 6,383,135 B1
(45) Date of Patent: May 7, 2002

(54) SYSTEM AND METHOD FOR PROVIDING SELF-SCREENING OF PATIENT SYMPTOMS

(76) Inventors: Oleg K. Chikovani, 16 Premiere Point, Newport Beach, CA (US) 92657; William R. Dobkin, 6020 Lido La., Long Beach, CA (US) 90803

( * ) Notice: Subject to any disclaimer, the term of this patent is extended or adjusted under 35 U.S.C. 154(b) by 0 days.

(21) Appl. No.: 09/505,974

(22) Filed: Feb. 16, 2000

(51) Int. Cl.[7] .................................................. A61B 5/00
(52) U.S. Cl. ........................ 600/300; 128/920; 128/904; 434/262; 705/3
(58) Field of Search ................................. 600/200–301, 600/300; 128/903, 904, 920–925; 705/2, 3; 434/262–275

(56) References Cited

U.S. PATENT DOCUMENTS 6,206,829 B1 * 10/2001 Iliff ............................ 600/300

* cited by examiner

Primary Examiner—Kevin Shaver
Assistant Examiner—Michael C Astorino
(74) Attorney, Agent, or Firm—Kenneth W. Float

(57) ABSTRACT

A medical self-screening system and method that allows rapid triage of patient medical problems. An exemplary system includes a computer having a selection device, a display, and an optional printer. A storage device containing one or more databases is coupled to the computer. Triage software runs on the computer that generates and displays a symptom screen display comprising a pictorial image of the body containing selectable regions that may be affected by patient symptoms. The patient selects a generally affected area or region on the displayed anatomical picture of the body using the selection device. Then the triage software displays a subsequent anatomical picture which is an enlarged more detailed view of the affected area. The patient selects a more specific region of the affected area shown in the enlarged view. The triage software then displays symptom selection screens that permit comparison of groups of symptoms experienced by the patient. The selected symptoms and data derived from the one or more databases are processed to determine an appropriate course of action that should be taken by the patient. The appropriate course of action is displayed to the patient.

18 Claims, 6 Drawing Sheets

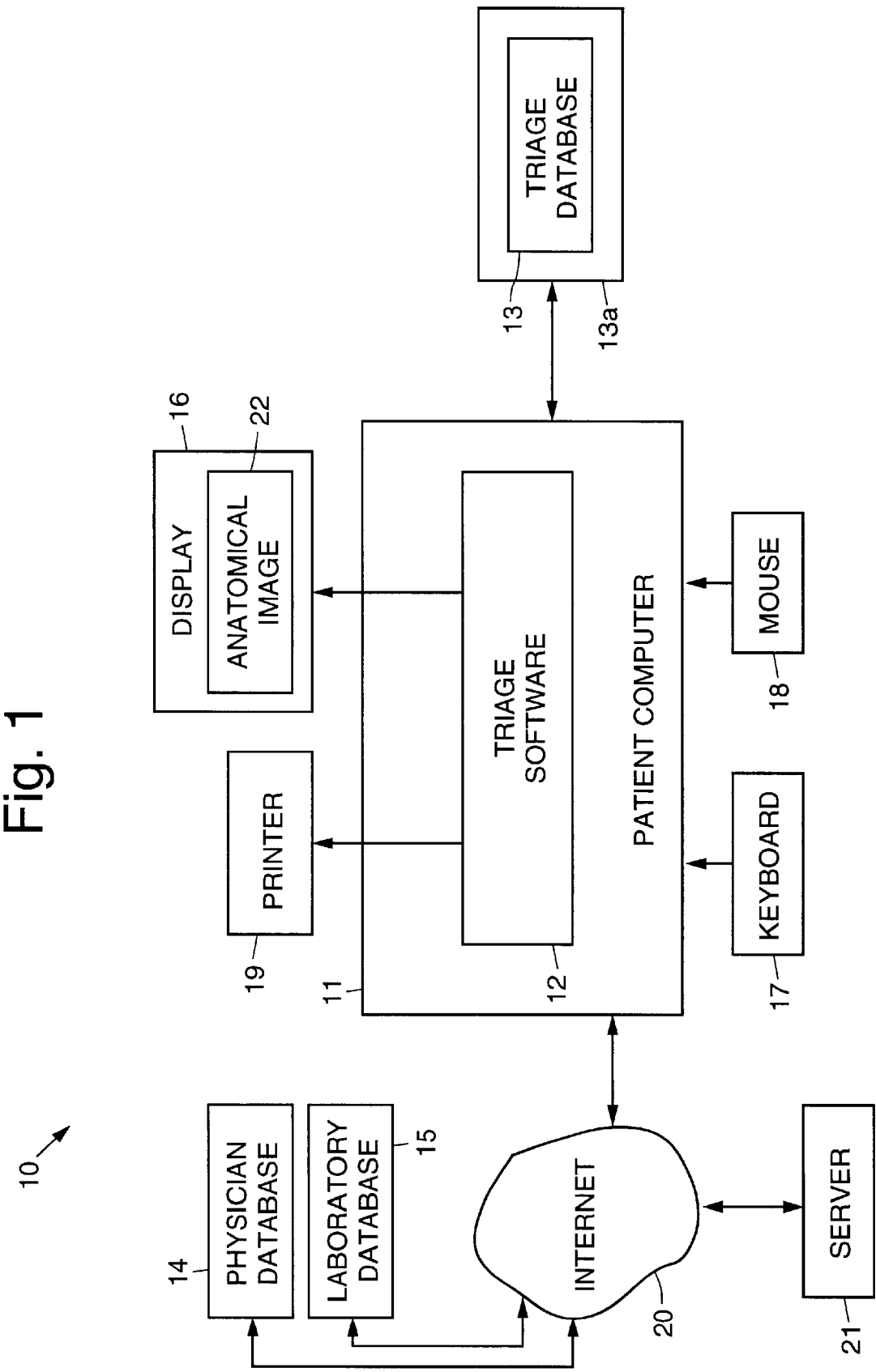

Fig. 2

E-TRIAGE.NET™
YOUR ELECTRONIC GP ™

BY IDENTIFYING SYMPTOMATIC AREAS FROM PICTORIAL DISPLAYS, E-TRIAGE.NET, THROUGH A CAREFULLY-CONSTRUCTED SERIES OF PATHWAYS DESIGNED BY LEADING SPECIALISTS FROM ALL AREAS OF MEDICINE, YOU CAN RAPIDLY ANALYZE YOUR SYMPTOMS. THIS INFORMATION WILL BE USED TO DETERMINE WHAT TESTS YOU REQUIRE AND WHAT TYPE OF MEDICAL SPECIALIST OR GENERALIST YOU NEED TO SEE. THIS SYSTEM IS DESIGNED TO ALLOW YOU TO QUICKLY EVALUATE YOUR MEDICAL PROBLEMS. NO LONGER WILL YOU NEED MULTIPLE OFFICE VISITS TO INITIATE THE RIGHT MEDICAL CARE. LONG WAITS IN OFFICES AND DELAYS IN OBTAINING NEEDED TESTS WILL BE STREAMLINED.

LAST NAME: [ ] FIRST NAME: [ ]
HOME PHONE NUMBER: [ ] SSN: [ ]
HOME ADDRESS: [ ]
E-MAIL ADDRESS: [ ]
HMO AFFILIATION: [ ]
IPA AFFILIATION: [ ]
INSURANCE GROUP NUMBER: [ ]
PRIMARY CARE PROVIDER: [ ]

E-TRIAGE.NET™
YOUR ELECTRONIC GP ™

BASED ON THE INFORMATION WHICH YOU HAVE PROVIDED, THE FOLLOWING TESTS SHOULD BE DONE:

1. 
2. 
3.

BASED ON THE INFORMATION WHICH YOU HAVE PROVIDED YOU SHOULD SEE THE FOLLOWING SPECIALIST OR GENERAL PRACTITIONER.

PHYSICIAN:
ADDDRESS:
TELEPHONE NO:

IT HAS BEEN OUR PLEASURE TO HELP YOU EVALUATE YOUR MEDICAL PROBLEMS. WE HOPE THAT THIS WILL EXPEDITE YOUR CARE AND HELP YOU RECOVER AS QUICKLY AS POSSIBLE. IF YOU HAVE ANY SUGGESTIONS, PLEASE LET US KNOW AT OUR EMAIL SITE, E-TRIAGE.NET.

END

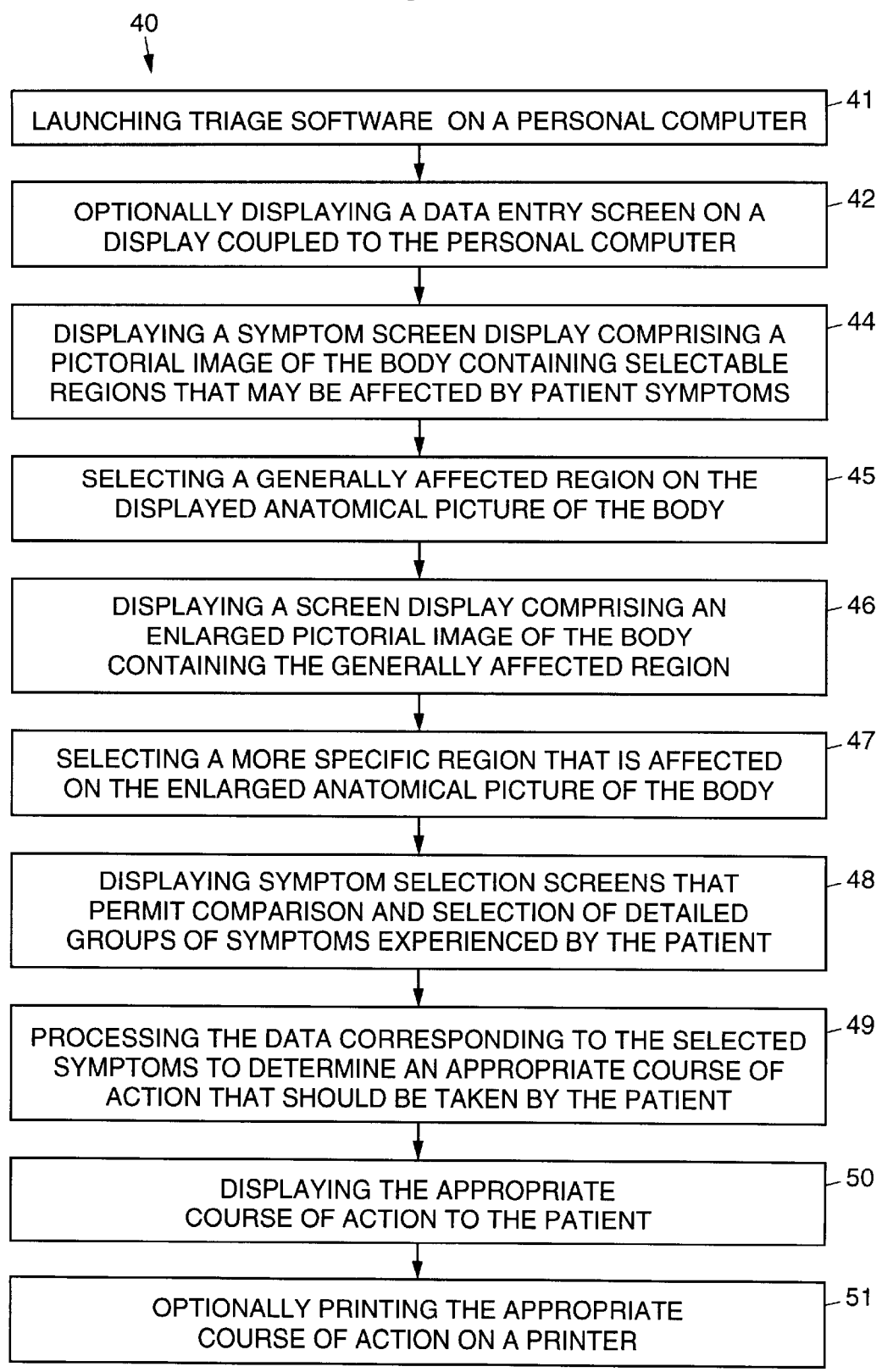

SYSTEM AND METHOD FOR PROVIDING SELF-SCREENING OF PATIENT SYMPTOMS

BACKGROUND

The present invention relates to systems and methods for evaluating patient illnesses, and more particularly to an system and method that provides the ability for a patient to personally evaluate his or her symptoms to determine appropriate tests that should be taken and treatment physicians that should be seen.

The practice of medicine has been relatively slow to embrace the information revolution. However, there is no system in so great a need of renovation to handle the endless data than the practice of medicine in the United States. The individualistic basis of medicine has also limited the availability of data and any uniformity of data management. There is constant duplication of services between hospitals, doctor's offices, labs and ancillary support facilities. This redundancy, by itself, drastically keeps costs high and for the individual practitioner represents a monumental task.

Within this system, the patient often feels neglected. When serious medical conditions arise, it is often an ordeal to obtain the correct diagnosis and treatment. Moreover, there are constant bottlenecks often intended to delay or avoid needed care. These delays can lead to increased pain, prolonged medical conditions or more serious medical sequelae. In addition, the psychological impact of delays in identifying and treating disease adversely affects not only outcome, but also consumer satisfaction.

Heretofore, it has become doctrine, within the United States, that systems designed to limit access were the only ways to control ever rising medical costs. Unfortunately, it often placed the physician in an adversarial position with the patient. Furthermore, the physician and hospital often benefited financially from limiting services or supplies.

The art and science of medicine has always depended on the sacred relationship formed between the patient and the physician. This relationship provides for more than just scientific treatment, it engender trust and faith. In addition, the practice of medicine has always championed individualism, even though the care of every patient is a team endeavor. The evolution of HMO medicine has served to limit access to specialists and tests. The system became focused on profits, no longer placing the patient at the center of attention. The inventors believe that this is a fatal flaw in the current medical system.

Heretofore, no existing system allows a patient to personally evaluate his or her medical condition and symptoms to determine what tests should be taken and what treatment physicians should be seen. Also, no existing system is available that allows patients to rapidly evaluate their symptoms, suggest tests and treatment physicians, and schedule such tests and physician office visits for consultation.

Accordingly, it would be advantageous to have an interactive system and method that allows a patient to personally evaluate his or her symptoms to determine tests that should be taken, and treatment physicians that should be seen.

SUMMARY OF THE INVENTION

The present invention provides for an medical self-screening system and method that allows rapid self-evaluation of patient medical problems. An exemplary medical self-screening system comprises a computer having a selection device, such as a keyboard and/or a mouse. The computer is coupled to a display and an optional printer. The computer comprises or is coupled to a storage device that stores one or more databases. The computer also comprises triage software that interfaces with the patient and the one or more databases on the storage device to allow the patient to evaluate his or her medical problem. The computer may also be connected to the Internet which allows access to remote servers and databases The triage software used by the system and method preferably displays a two- or three-dimensional rendition of the body (anatomical picture), that illustrates possible areas that are affected with the patients symptoms. Using the selection device, the patient identifies the generally affected area or region on the anatomical picture of the body. Once a region is selected, a subsequent anatomical picture is displayed which is an enlarged view of the affected area. This allows the patient to more accurately visualize and identify the specific region where the symptoms are. The specifically selected region is also used to help determine the differential diagnosis and appropriate tests and referrals.

In addition, an important feature of the anatomical models, particularly the enlarged versions, is that specific areas of interest, where symptoms commonly occur, may be highlighted. This helps to draw the patient's attention to the correct area. These affected area is then clicked on with the mouse. A subsequent window or hyperlink may be used to display choices that pertain to that specific anatomical location.

Once these choices are made, a series of symptom boxes or screens are displayed. The symptom boxes or screens permit comparison of groups of symptoms, rather than one symptom at a time. By having various diagnostic groups of symptoms associated with symptom boxes or screens that are sufficiently different, the patient is able to effectively identify the correct set of symptoms. The appropriate tests, referrals and diagnostic possibilities are then determined and displayed to the patient and optionally printed.

More particularly, upon completion of the screen-based pictorial and symptom screens interrogation, data corresponding to the selections made by the patient are processed along with data contained in the one or more databases by the triage software using triage protocols that evaluate the patient symptoms to determine an appropriate course of action that should be taken by the patient. The one or more databases on the storage device store information relating to tests that may be performed and physicians or types of physicians that may be consulted. The appropriate data is retrieved by the triage software from the one or more databases on the storage device based upon the evaluation of the symptoms.

Appropriate courses of action include the immediate use of emergency medical services, recommended tests that should be performed, and an appropriate physician that should be consulted. More particularly, situations that require immediate care can be rapidly assessed and the patient can be directed appropriately to emergency medical services. All other situations have recommendations made as to what tests would be useful and what specialists or generalists should see the patient.

In a preferred embodiment, the triage software runs independently on the computer, and interacts with the one or more databases, that store information relating to tests that may be performed and physicians that may be consulted. Alternatively, the triage software can run as a web site, interacting with its own database and remotely-located databases maintained by insurance companies, health providers, and independent physician associations (IPAs), for example.

Using the present medical self-screening system and method, patients do not have to wait for appointments to evaluate their medical problems. Their diseases will be diagnosed earlier. Early diagnosis limits progression of severe illnesses. All of this leads to more rapid and effective institution of treatment. Not only should the patients have better outcomes, but they will have far less psychological stress and suffer less.

History has shown repeatedly that well designed clinical protocols within the leading hospitals of our country actually lead to improved outcomes and decreased costs. The rapid and efficient use of necessary services enhances patient outcomes. Rapid involvement of the medical system, initiated by patients, will allow physicians to be more efficient and improve the services their patient's require. Costs are controlled through efficient use of the medical self-screening system and method. Diseases will be treated earlier and more effectively, thereby saving money.

BRIEF DESCRIPTION OF THE DRAWINGS

The various features and advantages of the present invention may be more readily understood with reference to the following detailed description taken in conjunction with the accompanying drawings, described by way of example, and wherein like reference numerals designate like structural elements, and in which:

FIG. 1 illustrates an exemplary medical self-screening system in accordance with the principles of the present invention;

FIG. 2 illustrates an exemplary data input screen display that may be presented to a patient using the system of FIG. 1;

FIG. 5 illustrates exemplary data that are displayed to the patient; and

FIG. 6 is a flow diagram that illustrates an exemplary medical self-screening method in accordance with the principles of the present invention.

DETAILED DESCRIPTION

Figure 3:
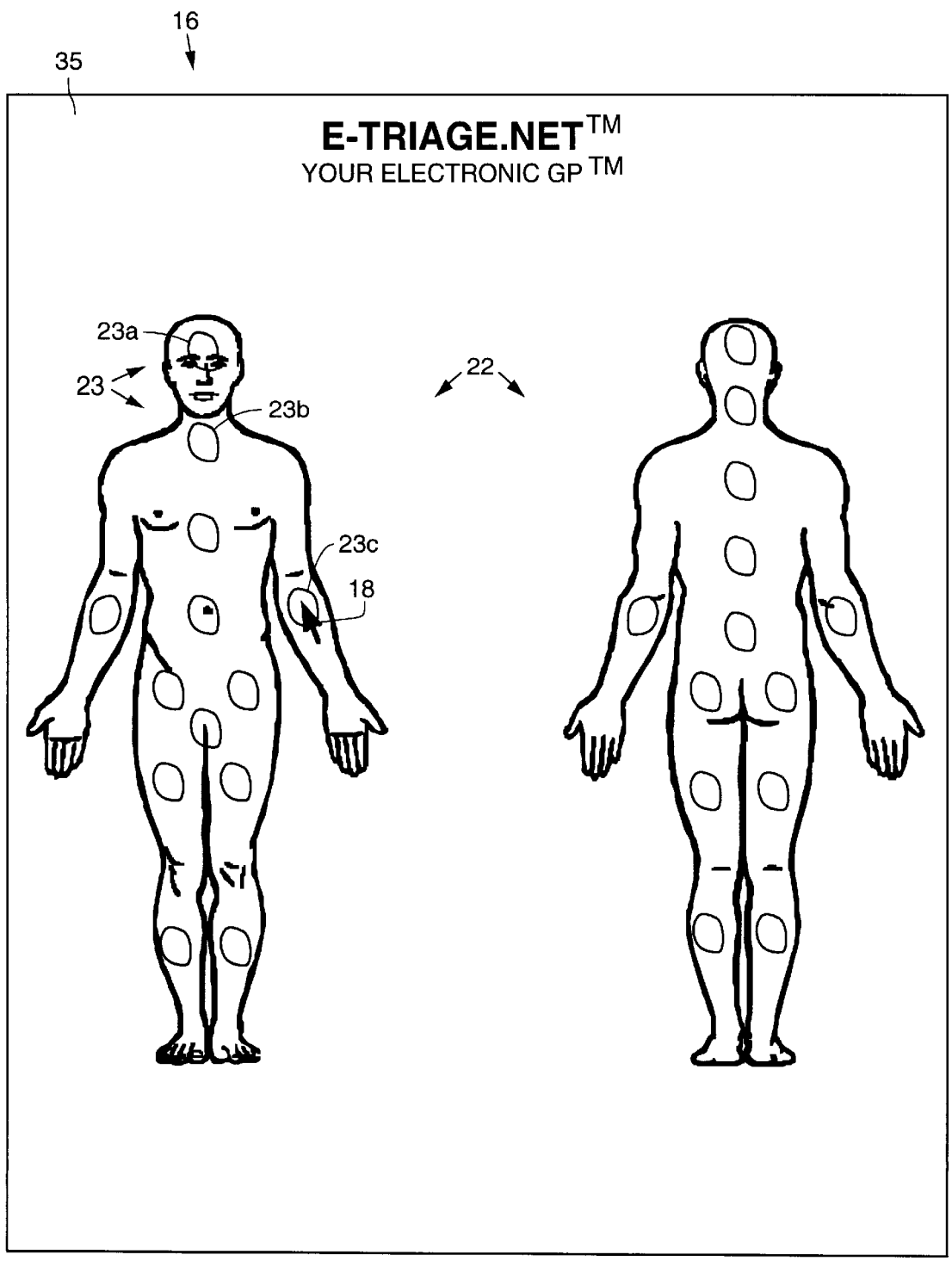
FIGS. 3 and 4 illustrate exemplary screen displays that are presented to a patient using the system of FIG. 1.

Referring to the drawing figures, FIG. 1 illustrates an exemplary medical self-screening system 10 in accordance with the principles of the present invention. The medical self-screening system 10 provides for rapid medical self-screening and triage of patient medical problems. The exemplary medical self-screening system 10 comprises a patient computer 11 that is coupled to a display 16, and optionally to a printer 19. A keyboard 17 and a mouse 18 are also coupled to the patient computer 11. The patient computer 11 comprises a storage device 13a that stores one or more databases 13, illustrated as a triage database 13. The patient computer 11 comprises triage software 12 that interfaces with the one or more databases 13.

The patient computer 11 may also be connected to the Internet 20 which allows access to remote databases such as a remotely located physician database 14 or laboratory database 15. The remotely-located databases 14, 15 are typically maintained by insurance companies, health providers, and independent physician associations (IPAs), for example.

The connection to the Internet 20 also provides access to a remote server 21, such as is disclosed in U.S. patent application Ser. No. 09/497,738, filed Feb. 4, 2000, entitled "System And Method for Interactively Providing Patient Evaluation and Treatment Referral", the contents of which are incorporated herein by reference. The remote server 21 comprises a web-based version of the triage software and has or is coupled to the remotely-located databases 14, 15 and permits access by the triage software 12 to these data sources.

The triage database 13 may be used to store information regarding the patient including personal information, insurance information, health provider information, along with data relating to symptoms and evaluation that are used during patient screening and triage. The remotely-located physician database 14 provides a list of referral physicians, including names, specialty (if any), addresses, telephone numbers. The remotely-located laboratory database 18 may be used to store information relating to testing laboratories, such as clinical laboratories that perform blood tests, urinalysis, or other chemical-related tests, or diagnostic testing facilities that perform brain scans, magnetic resonance imaging, and X-ray tests, for example.

FIG. 2 illustrates an exemplary data input screen display 34 that may be presented to a patient using the system 10 of FIG. 1. The initial data entry screen display 34, if displayed, instructs the patient regarding the information that is to be input and what information will be provided by the medical self-screening system 10. The initial data entry screen display 34 elicits biographic data regarding the patient, such as name, address, social security number, insurance information, and health provider information, for example. When these questions are answered, clicking on a Continue button 32 links to the main symptom screen display 35 (FIG. 3)

Figure 4:
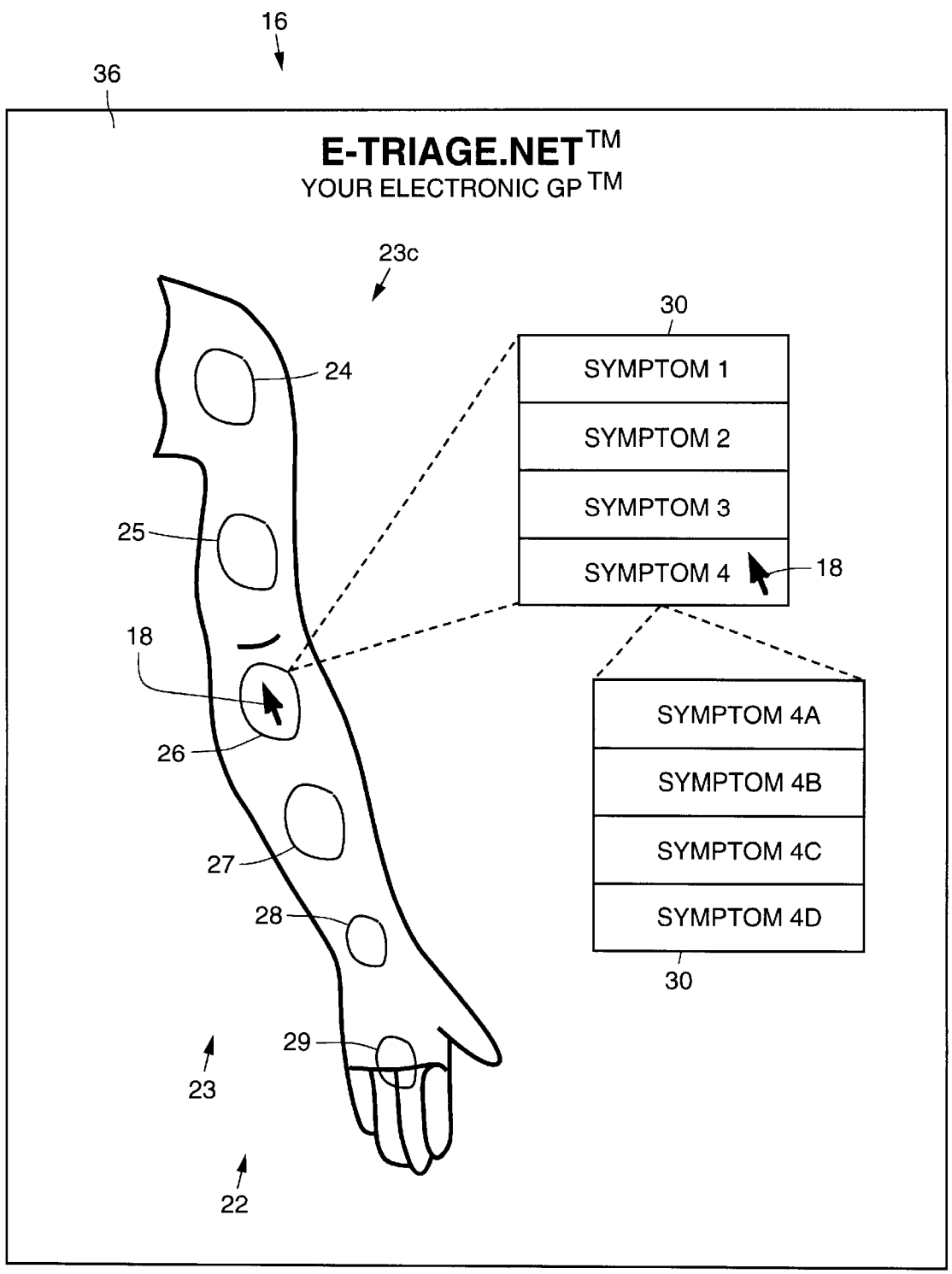

FIGS. 3 and 4 illustrate exemplary screen displays 36, 37 that may be presented to a patient using the system 10 of FIG. 1. Referring to FIG. 3, the triage software 12 used by the system 10 preferably displays a two- or three-dimensional anatomical picture 22 or image 22 of the body, which illustrates possible areas 23 that are affected with the patients symptoms. Using the mouse 18, the patient identifies the generally affected area 23 or region on the anatomical picture 22 of the body. Different areas 23 of the body may be selected including the head area 23a, neck area 23b, arm area 23c, and so forth. FIG. 3 illustrates that the patients left arm was selected which is shown by the cursor pointing at the arm area 23c.

It is to be understood, however, that the screen displays 36, 37 may be configured in a variety of forms and that the anatomical picture 22 shown in FIG. 4 is intended to illustrate the symptom identification process that is undertaken by the patient using the system 10 and the type of data that is input by the patient. Thus, the specific form of the screen displays 36, 37 shown in FIGS. 3 and 4 should not be considered as limiting the present invention.

Once an area 23 is selected, such as the arm area 23c, a subsequent anatomical picture (FIG. 4) is displayed which is an enlarged view of the affected area 23c. This allows the patient to more accurately visualize and identify the specific area 23 (the arm area 23c) where the symptoms are. The specifically selected area 23c is also used to help determine the differential diagnosis and appropriate tests and referrals. This will be described in more detail below.

In addition, an important feature of the anatomical pictures 22, particularly the enlarged versions, such as is shown in FIG. 4, is that specific area 23c of interest, where symptoms commonly occur, may be highlighted. This is illustrated in FIG. 4 by encircled areas 24–29. The areas that are highlighted may include the shoulder area 24, upper arm area 25, elbow area 26, lower arm area 27 wrist area 27 and hand area 29, for example. The highlighting helps to draw the patient's attention to the correct area 22. The affected area, such as the elbow area 26, for example, is then clicked on with the mouse 18.

The subsequent display (or hyperlink), such as the subsequent anatomical picture shown in FIG. 4, may then be used to display choices that pertain to that specific anatomical area 22. For example, a series of symptom boxes 30 or screens 30 may be displayed that allow additional choices to be made. For example a series of pull-down menus 31, 32 may be sequentially displayed, or links to additional screens, for example, that allow the patient to select the appropriate symptoms that he or she is experiencing. Each successive screen display is more specifically related to the patient's specific illness and medical history, based upon selections made in previous symptom screen display 33.

The symptom boxes 30 or screens 30 permit comparison of groups of symptoms, rather than one symptom at a time. By having various diagnostic groups of symptoms that are sufficiently different associated with the displayed symptom boxes 30 or screens 30, the patient is able to effectively identify the correct set of symptoms.

The appropriate tests, referrals and diagnostic possibilities are then determined and displayed to the patient and optionally printed. More particularly, upon completion of the screen-based pictorial and symptom screen interrogation, data corresponding to the selections made by the patient are processed by the triage software 12 using triage protocols that evaluate the patient symptoms and interface with the one or more databases 13 to determine an appropriate course of action that should be taken by the patient. The one or more databases 13 store information relating to tests that may be performed and physicians or types of physician that may be consulted. This information is provided to the patient.

An exemplary symptom evaluation relating to the nervous system displays various symptoms using illustrations and pull-down menus, for example. Successive symptom screen displays present pull-down menus may or illustrations for: headache, blurred or double vision, decreased hearing, tinnitus or vertigo, swallowing difficulties, speech or reading problems, weakness, numbness or parathesias, nausea or vomiting, stiff neck, neck or back pain, radiating pain into extremities, bladder or bowel incontinence, and seizures.

The system 10 and triage software 12 thus allow the patient to easily input his or her significant symptoms and medical history by simply selecting locations in illustrations (and by using pull-down menus) which generate data that is processed by the triage software 12. Upon completion of the screen-based interrogation, the triage software 12 processes the data.

The triage software 12 embodies triage protocols that evaluate the patient data to determine an appropriate course of action that should be taken by the patient regarding his or her medical condition. The triage protocols relate to the following areas: nervous system; ears, nose and throat; cardiac; pulmonary; gastrointestinal; urological; sexual; psychiatric; musculoskeletal; and blood.

Appropriate courses of action that are determined by the triage software 12 include immediate emergency medical services, recommended tests that should be performed, and an appropriate type of physician or a particular physician that should be consulted. More particularly, situations that require immediate care can be rapidly assessed and the patient can be directed appropriately to emergency medical services. All other situations have recommendations made as to what tests would be useful and what specialists or generalists should be seen the patient.

The recommendations derived from the processing performed by the triage software 12 are displayed to the patient. An exemplary output screen display 37 is illustrated in FIG. 5. The patient is thus informed of an appropriate course of action given his or her current medical situation. The tests that should be performed, and the type of physician that should be consulted are displayed. Clicking on an End button 38, for example, terminates the evaluation process.

As was mentioned above, the connection to the Internet 20 also provides access to the remote server 21, which comprises the web-based version of the triage software. The remote server 21 comprises or is coupled to the remotely-located databases 14, 15 and permits access by the triage software 12 to these data sources. In this case, additional information may be provided to the patient using the system 10.

More particularly, and as is described in more detail in the referenced patent application, interfacing to the remote server 21 allows the triage software 12 to retrieve and display the location and telephone number of a test location, an authorization number authorizing the test, and physician's name, address and telephone number (or a list of suitable physicians). In the event that tests are suggested, the tests may be immediately scheduled and a follow-up appointment with the appropriate physician scheduled to review the results of the tests.

Interfacing to the server computer 21 allows forwarding of prescriptions to testing laboratories to order recommended tests derived from the processing performed the triage software 12. Also, information may be forwarded to the physician that is to see the patient based upon results of the processing performed the triage software 12. An electronic medical file that includes patient biographical information, medical history, and results of the interactive triage of the patient, for example, may be forwarded to the physician that is to see the patient.

Use of the medical self-screening system 10 and the clinical protocols contained in its triage software 12 to provide interactive patient evaluation should lead to improved outcomes and decreased costs. The medical self-screening system 10 thus improves patient care by allowing early evaluation of patient medical problems and suggesting appropriate test and physicians that may treat the problem in a timely manner. By using the medical self-screening system 10, diseases will be treated earlier and more effectively, thus saving money.

FIG. 6 is a flow diagram that illustrates an exemplary medical self-screening method 40 in accordance with the principles of the present invention. The exemplary medical self-screening method 40 comprises the following steps.

A patient launches 41 a triage software 12 on a personal computer 11. The triage software 12 optionally displays 42 an initial data entry screen 34 on a display 16 coupled to personal computer 11. The initial data entry screen 34 allows the patient to optionally enter 43 biographic and provider data, such as name, address, social security number, insurance information, and health provider information.

A main symptom screen display 35 is then displayed 44 that presents one or more two- or three-dimensional anatomical pictures 22 or images 22 of the body. Possible areas 23 that may be affected with the patients symptoms are preferably highlighted. Using a mouse 18 or other control device, the patient selects 45 a generally affected area 23 or region on the displayed anatomical picture 22 of the body. After the affected area 23 is selected 45, a subsequent anatomical picture 22 is displayed 46 which is an enlarged more detailed view of the affected area 23.

A more specific region of the affected area 23 shown in the enlarged view is then selected 47, such as by using the mouse 18. Selection of the more specific region displays 48 one or more symptom boxes 30 or screens 30 that allow additional symptoms to be identified relating to the specifically affected area. For example a series of pull-down menus 31, 32, or links to additional screens 30, for example, may be sequentially displayed 48 that allow the patient to select the appropriate symptoms that he or she is experiencing. The symptom boxes 30 (or additional screens 30) permit comparison of groups of symptoms by the patient which most efficiently allows identification of the correct set of symptoms.

Once all displayed symptoms have been identified, the triage software 12 processes 49 the selected symptom data along with data derived from the one or more databases 13 to determine an appropriate course of action that should be taken by the patient. More particularly, upon completion of the screen-based pictorial and symptom screen interrogation, data corresponding to selections made by the patient are processed 49 by the triage software 12 using triage protocols that evaluate the patient symptoms to determine an appropriate course of action that should be taken by the patient. The one or more databases 13 on the storage device 13*a* store information relating to tests that may be preformed and physicians or types of physicians that may be consulted. The appropriate data is retrieved by the triage software 12 from the one or more databases 13 on the storage device 13*a* based upon the evaluation of the symptoms.

The appropriate tests, referrals and diagnostic possibilities are then determined and displayed 50 to the patient and may be optionally printed 51. The tests that may be performed and physicians or types of physicians that should be consulted are retrieved from the one or more databases 13 and are displayed 50 and may be optionally printed 51 by the patient.

Thus, medical self-screening systems and methods that evaluate patient symptoms and recommend appropriate tests and treatment physicians based upon the evaluation have been disclosed. It is to be understood that the described embodiments are merely illustrative of some of the many specific embodiments that represent applications of the principles of the present invention. Clearly, numerous and other arrangements can be readily devised by those skilled in the art without departing from the scope of the invention.

What is claimed is:

1. A medical self-screening system comprising:
   a computer comprising a selection device and a display;
   a storage device containing one or more databases coupled to the computer, and
   triage software that runs on the computer that is operable to generate and display one or more anatomical pictures of the body containing areas that may be affected with the patient's symptoms, to allow selection of a generally affected area on the displayed anatomical picture using the selection device, to display a subsequent anatomical picture which is an enlarged view of the affected area, to allow selection of a specific affected area on the enlarged view of the affected area using the selection device, to display one or more symptom screens that allow additional symptoms to be identified relating to the specifically affected area using the selection device, and that processes the selected symptoms and interfaces with the one or more databases to determine an appropriate course of action that should be taken by the patient, and that displays the appropriate course of action to the patient.

2. The system recited in claim 1 wherein the one or more symptom screens permit comparison of groups of symptoms by the patient which most efficiently allows identification of the correct set of symptoms.

3. The system 10 recited in claim 1 wherein the appropriate course of action selectively comprises the immediate use of emergency medical services, recommended tests that should be performed, and an appropriate physician that should be consulted.

4. The system recited in claim 1 wherein the triage software comprises triage protocols that evaluate the data to determine the appropriate course of action that should be taken by the patient.

5. The system recited in claim 1 wherein the triage protocols are selected from the group consisting of the nervous system; ears, nose and throat; cardiac; pulmonary; gastrointestinal; urological; sexual; psychiatric; musculoskeletal; and blood.

6. The system recited in claim 1 further comprising a printer coupled to the computer that generates a printed output of the appropriate course of action that should be taken by the patient determined by the triage software.

7. The system recited in claim 1 further comprising one or more databases that selectively store personal information, insurance information, health provider information, referral physician information, test laboratory information, and data relating to symptoms and evaluation.

8. The system recited in claim 1 wherein the triage software displays an initial data entry screen that allows the patient to enter biographic and provider information.

9. The system recited in claim 1 wherein the computer is coupled by way of the Internet to a remote server that interfaces to one or more remotely-located databases, and wherein the triage software retrieves, processes and displays data stored on the one or more remotely-located databases.

10. The system recited in claim 9 wherein the triage software retrieves and displays the location and telephone number of a test location, and a name, address and telephone number of a physician that is to be consulted.

11. The system recited in claim 9 wherein the triage software forwards prescriptions to testing laboratories to order recommended tests.

12. The system recited in claim 9 wherein the triage software forwards an electronic medical file that includes patient biographical information, medical history, and results of the interactive triage of the patient to the physician that is to see the patient.

13. A medical self-screening method for use in triaging a patient, comprising the steps of:
   launching triage software on a computer having a selection device and a display, and which is coupled to a storage device containing one or more databases;
   displaying a symptom screen display comprising a pictorial image of the body, containing selectable regions that may be affected by patient symptoms;
   selecting a generally affected area or region on the displayed anatomical picture of the body;
   displaying a subsequent anatomical picture which is an enlarged more detailed view of the affected area;
   selecting a more specific region of the affected area shown in the enlarged view;

displaying symptom selection screens that permit comparison of groups of symptoms experienced by the patient;

processing the selected symptoms and data derived from the one or more databases to determine an appropriate course of action that should be taken by the patient; and displaying the appropriate course of action to the patient.

14. The method recited in claim 13 wherein the selectable regions are highlighted.

15. The method recited in claim 13 further comprising the step of printing the appropriate course of action that should be taken by the patient determined by the triage software.

16. The method recited in claim 13 wherein the appropriate course of action selectively includes the immediate use of emergency medical services, recommended tests that should be performed, and an appropriate physician that should be consulted.

17. The method recited in claim 13 wherein the triage software comprises triage protocols that evaluate the data to determine the appropriate course of action that should be taken by the patient.

18. The method recited in claim 17 wherein the triage protocols are selected from the group consisting of the nervous system; ears, nose and throat; cardiac; pulmonary; gastrointestinal; urological; sexual; psychiatric; musculoskeletal; and blood.

\* \* \* \* \*